US006942876B2

(12) United States Patent
Magnus-Miller et al.

(10) Patent No.: US 6,942,876 B2
(45) Date of Patent: Sep. 13, 2005

(54) ANALGESIC COMPOSITIONS COMPRISING ANTI-EPILEPTIC COMPOUNDS AND METHODS OF USING SAME

(75) Inventors: Leslie Magnus-Miller, Livingston, NJ (US); Douglas A. Saltel, Summit, NJ (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/075,929

(22) Filed: Feb. 13, 2002

(65) Prior Publication Data

US 2003/0065028 A1 Apr. 3, 2003

Related U.S. Application Data

(62) Division of application No. 09/463,116, filed as application No. PCT/US98/17083 on Aug. 18, 1998, now Pat. No. 6,593,368.
(60) Provisional application No. 60/058,207, filed on Sep. 8, 1997.

(51) Int. Cl.[7] .............................. A61K 9/14; A61K 9/20; A61K 9/48
(52) U.S. Cl. .................... 424/464; 424/451; 424/489
(58) Field of Search .......................... 424/451, 455, 424/456, 464, 465, 468, 489, 457

(56) References Cited

U.S. PATENT DOCUMENTS

| 4,024,175 A | 5/1977 | Satzinger et al. |
| 4,087,544 A | 5/1978 | Satzinger et al. |

(Continued)

FOREIGN PATENT DOCUMENTS

| BE | 634N102 A | 12/1963 |
| CN | 1110141 A | 10/1995 |

(Continued)

OTHER PUBLICATIONS

Shimoyama et al., "Gabapentin enhances the antinociceptive effects of spinal morphine in the rat tail–flick test", Pain, vol. 72, 1997, pp. 375–382.
Wetzel et al., "Use of Gabapentin in Pain Management", The Annals of Pharmacology, vol. 31, 1997, pp. 1082–1083.
Theodore W. Rall, et al., "Drugs Effective in the Therapy of the Epilepsies", The Pharmacological Basis of Therapeutics, 8th Ed., Editors Alfred Goodman Gilman, MD, Ph.D., Theodore W. Rall, Ph.D., D.Med., Alan S. Nies, MD, and Palmer Taylor, Ph.D., copyright 1990, pp. 436–462, Pergamon Press, NY, NY.
Rosner, et al., "Gabapentin Adjunctive Therapy in Neuropathic Pain States" The Clinical Journal of Pain, 1996;12:56–58.

(Continued)

Primary Examiner—James M. Spear
(74) Attorney, Agent, or Firm—David R. Kurlandsky; Claude F. Purchase, Jr.; Steven R. Eck

(57) ABSTRACT

The present invention is directed to novel combinations of anti-epileptic compounds that demonstrate pain alleviating properties, with compounds selected from the group consisting of analgesics, NMDA receptor antagonists, and NSAIDs and pharmaceutical compositions comprising same. It has been discovered that the administration of anti-epileptic compounds that demonstrate pain alleviating properties in these novel combinations results in an improved reduction in the frequency and severity of pain. It is also believed that the incidence of unwanted side effects can be reduced by these novel combinations in comparison to using higher doses of a single agent treatment to achieve a similar therapeutic effect. The present invention is also directed to methods of using effective amounts of the novel pharmaceutical compositions to treat pain in mammals.

10 Claims, 2 Drawing Sheets

U.S. PATENT DOCUMENTS

| | | | |
|---|---|---|---|
| 5,234,929 A | 8/1993 | Chelen | 514/269 |
| 5,321,012 A | 6/1994 | Mayer et al. | 514/25 |
| 5,352,638 A | 10/1994 | Beall et al. | 510/10 |
| 5,420,270 A | 5/1995 | Chandrakumar et al. | 540/488 |
| 5,466,823 A | 11/1995 | Talley et al. | |
| 5,556,838 A | 9/1996 | Mayer et al. | 514/25 |
| 5,563,175 A | 10/1996 | Silverman et al. | |
| 6,001,876 A | 12/1999 | Singh | |
| 6,057,373 A | 5/2000 | Fogel et al. | |
| 6,127,418 A | 10/2000 | Bueno et al. | |
| 6,187,338 B1 * | 2/2001 | Caruso et al. | 424/468 |
| 6,197,819 B1 | 3/2001 | Silverman et al. | |
| 6,242,488 B1 | 6/2001 | Bueno et al. | |
| 6,406,716 B2 | 6/2002 | Caruso et al. | |
| 6,426,368 B2 | 7/2002 | Bueno et al. | |
| 6,451,857 B1 | 9/2002 | Hurtt et al. | |
| 6,593,368 B2 | 7/2003 | Magnus-Miller et al. | |

FOREIGN PATENT DOCUMENTS

| | | |
|---|---|---|
| DE | 1966802 A | 4/1974 |
| GB | 2255279 A | 11/1992 |
| JP | 54110334 A | 8/1979 |
| JP | 61221121 A | 10/1986 |
| JP | 6100468 A | 4/1994 |
| JP | 6227969 A | 8/1994 |
| WO | 8701036 A | 2/1987 |
| WO | WO 87/01036 | 2/1987 |
| WO | 8905642 A | 6/1989 |
| WO | WO 89/05642 | 6/1989 |
| WO | WO 93/23383 A1 | 11/1993 |
| WO | 9607412 A1 | 3/1996 |
| WO | 9807447 | 2/1998 |
| WO | WO 98/07447 | 2/1998 |
| WO | WO 99/08670 A1 | 2/1999 |
| WO | WO 99/08671 A1 | 2/1999 |

OTHER PUBLICATIONS

PCT International Search Report PCT/US98/17083.

Kathryn J. Elliot, "New Analgesics Emerge From Pain Pathogenesis Research", Oncology News International, Apr. 1997, pp 14–15.

Gary Mellick, et al., "The Use of Gabapentin in the Treatment of Reflex Sympathetic Dystrophy and a Phobic Disorder", American Journal of Pain Management, vol. 5, No. 1, Jan. 1995, pp 7–9.

Y Miyamoto, et al., "Antinociceptive Synergism Between Supraspinal and Spinal Sites After Subcutaneous Morphine Evidenced by CNS Morphine Content", Brain Research, 552, 19991, pp 136–140.

Howard Rosner, et al., "Gabapentin Adjunctive Therapy in Neuropathic Pain States", The Clinical Journal of Pain, vol. 12, No. 1, 1996, pp 56–58.

Steven C. Schachter, et al., "Treatment of Central Pain with Gabapentin Case Reports", J. Epilepsy, vol. 9, No. 3, 1996, pp 223–224.

Alan Z. Segal, et al., "Gabapentin as a Novel Treatment for Postherpetic Nuralgia", Neurology, Vo. 46, Apr. 1996, pp 1175–1176.

Megumi Shimoyama, et al., "Gabapentine Enhances the Antiociceptive Effects of Spinal Morphine in the Rat Tail–flick Test", Pain, vol. 72, 1997, pp 375–382.

Ronald J. Tallarida, et al., Statistical Analysis of Drug–Drug and Site–Site Interactions with Isobolograms, Life Sciences, vol. 45, 1989, pp 947–961.

Ronald J. Tallarida, "Statistical Analysis of Drug Combinations for Synergism", Pain, vol. 49, 1992, pp 93–97.

Ronald J. Tallarida et al., "Testing for Synergism Over a Range of Fixed Ratio Drug Combinations: Replacing the Isobologram", Life Sciences, vol. 58, No. 2, 1996, pp 23–28.

John J. Zapp, "Postpoliomyelitis Pain Treated with Gabapentin", American Family Physician, vol. 53, No. 8, Jun. 1996, pp 2442–2445.

Wetzel, et al, "Use of gabapentin in pain management", Ann. Pharmacother., 1997; 31(9): pp 1082–1083 CODEN:APHRER; ISSN:1060–0280.

Stanfa, et al, "Gabapentin, ineffective in normal rats, markedly reduces C–Fiber evoked response after inflammation", NeuroReport, 1997; 8(3); pp 587–590. CODEN:NERPEZ; ISSN:0959–4965.

* cited by examiner

ANALGESIC COMPOSITIONS COMPRISING ANTI-EPILEPTIC COMPOUNDS AND METHODS OF USING SAME

CROSS-REFERENCE TO RELATED APPLICATIONS

This patent application is a divisional application under 35 U.S.C. § 121 of U.S. patent application Ser. No. 09/463,116, filed Jan. 18, 2000, now U.S. Pat. No. 6,593,368, issued Jul. 15, 2003, which is a 35 U.S.C. §371 application from PCT International Patent Application No. PCT/US98/17083, filed Aug. 18, 1998, which claims benefit of priority from U.S. Provisional Patent Application No. 60/058,207, filed Sep. 8, 1997.

FIELD OF THE INVENTION

The present invention is directed to novel combinations of anti-epileptic compounds that demonstrate pain alleviating properties, with compounds selected from the group consisting of analgesics, N-methyl-D-aspartate (NMDA) receptor antagonists and non-steroidal anti-inflammatory drugs (NSAIDs) and pharmaceutical compositions comprising same. It has been discovered that the administration of anti-epileptic compounds that demonstrate pain alleviating properties in these novel combinations results in an improved reduction in the frequency and severity of pain. It is also believed that the incidence of unwanted side effects can be reduced by these novel combinations in comparison to using higher doses of a single agent treatment to achieve a similar therapeutic effect. The present invention is also directed to methods of using effective amounts of the novel pharmaceutical compositions to treat pain in mammals.

BACKGROUND OF THE INVENTION

A number of treatments involving the administration of single drugs are currently recommended for pain relief The single administration of narcotic and non-narcotic analgesics and NSAIDs have been shown to display pain alleviating properties. Some anti-epileptics, such as gabapentin and pregabalin, have also demonstrated pain alleviating properties.

Despite the benefits derived from current single drug pain relief regimens, these regimens have disadvantages. One area of concern relates to the incidence of unwanted side effects caused by many of the pain treatment regimens available today. Narcotic analgesics, such as morphine, are sparingly prescribed for pain because of the well-known addictive effects and significant central nervous system (CNS) side effects and gastrointestinal side effects resulting from their single administration. Another class of drugs often used alone for treatment of pain, non-steroidal anti-inflammatory drugs, such as ibuprofen and naproxen, are criticized for their irritation of the gastrointestinal tract.

Another concern of current pain treatment regimens relates to their effectiveness. Many single active ingredients employed in current pain relief regimens cannot achieve adequate pain alleviation even at their maximum therapeutic approved doses in some severe pain states. In addition to not achieving adequate pain alleviation, increasing the drug dose may produce an increase in unwanted side effects such as cognitive impairment, nausea, and constipation.

In view of these concerns, it is evident that there is a need for an improved pain regimen that provides an improved therapeutic benefit (ie, reduced severity and/or frequency of pain) and/or reduces the incidence of unwanted side effects caused by many of the current regimens.

SUMMARY OF THE INVENTION

The inventors have now surprisingly found that anti-epileptic compounds having pain alleviating properties, when co-administered with compounds selected from the group consisting of analgesics, NMDA receptor antagonists, and NSAIDs, result in unexpected improved pain relief.

The present invention is directed to novel combinations for alleviating pain, the combinations comprising of anti-epileptic compounds, such as gabapentin and pregabalin, that have displayed pain alleviating properties, and compounds selected from the group consisting of NMDA receptor antagonists, analgesics, and NSAIDs. It is also believed that the incidence of unwanted side effects can be reduced by co-administration of these compounds with anti-epileptic compounds having pain alleviating properties in comparison to using higher doses of a single agent treatment to achieve a similar therapeutic effect.

The present invention is also directed to pharmaceutical compositions comprising the novel combinations of certain anti-epileptic compounds with compounds selected from the group consisting of NMDA receptor antagonists, analgesics, and NSAIDs. The active ingredients are combined with at least one pharmaceutically acceptable carrier. The novel pharmaceutical compositions are prepared in a wide variety of pharmaceutical delivery systems known to those of skill in the art, preferably oral and parenteral dosage forms.

The present invention is also directed to methods of treating mammals suffering from pain with the novel pharmaceutical composition to alleviate pain. The method comprises the step of administering the pharmaceutical compositions comprising the novel anti-epileptic combinations to mammals in need of pain relief

DETAILED DESCRIPTION OF THE INVENTION

Figure 1:
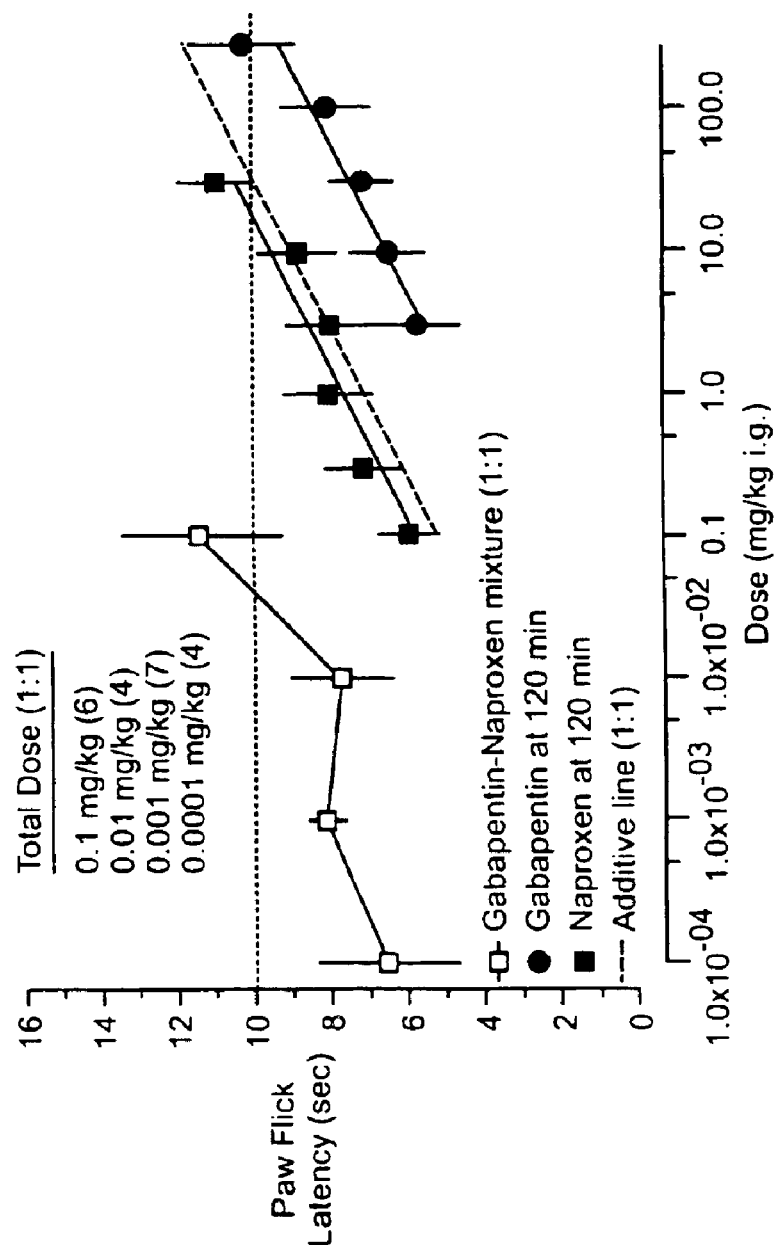
FIG. 1 shows the anti-hyperalgesic actions of fixed 1:1 (1 part by weight of gabapentin to 1 part by weight of naproxen sodium) combinations of gabapentin and naproxen sodium at various dosages.

It has now been unexpectedly found in accordance with the present invention that analgesic effects can be enhanced by the co-administration of anti-epileptic compounds that demonstrate pain alleviating properties together with compounds selected from the group consisting of analgesics, NSAIDs, and NMDA receptor antagonists. As used herein, the term "co-administration" is meant to include the administration of anti-epileptic compounds, before, during, or after administration of compounds selected from the group consisting of NMDA receptor antagonists, analgesics, and NSAIDs.

One advantage of using the novel combinations described herein is the reduced severity and/or frequency of pain. Another potential advantage is the overall improvement in pain control, which can include a reduction in the dosage and unwanted side effects.

Analgesics used in this invention can be, for example, non-narcotic analgesics or narcotic analgesic compounds.

Non-narcotic analgesics are generally defined to be those compounds that relieve pain without being addictive. A non-limiting example of a non-narcotic analgesic includes acetaminophen.

Narcotic analgesics are generally defined to be those compounds that are addictive when administered to treat a mammal for pain. Non-limiting examples of narcotic analgesics include opiates, opiate derivatives, opioids, and their pharmaceutically acceptable salts. Specific non-limiting examples of narcotic analgesics include alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, morphine, neperidine, phenomorphan, phenoperidine, piritradide, pholcodine, proheptazoine, properidine, propiran, racemoramide, thebacon, trimeperidine, and the pharmaceutically acceptable salts thereof.

NMDA receptor antagonists which can be used in the novel combination are compounds that block or reduce the effects of NMDA at the NMDA subclass of neuronal glutamate receptors. NMDA receptors are areas in the central nervous system that are selectively excited by NMDA and exert a biological effect when NMDA is bound to them. Non-limiting examples of NMDA receptor antagonists include dextromethorphan and ketamine.

The term "NSAID", as used to describe other compounds useful in the novel combination herein, is intended to be a non-steroidal anti-inflammatory compound. NSAIDs are categorized by virtue of their ability to inhibit cyclooxygenase. Cyclooxygenase 1 and cyclooxygenase 2 are the two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and sulindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxican. Other useful NSAIDs include aspirin.

Another class of NSAID has recently been described which selectively inhibits cyclooxygenase 2. These compounds reduce pain and inhibit the inflammatory response without damaging the gastric mucosa, a common toxicity observed with the mixed inhibitors. (Z)-5-[[3,5-bis(1,1-dimethylethyl)-4-hydroxyphenyl]methylene]-2-imino-4-thiazolidinone methanesulfonate (1:1), celecoxib, meloxicam, and their pharmaceutically acceptable salts are examples of selective cyclooxygenase 2 inhibitors.

The term "anti-epileptic compound" is generally defined to be a pharmaceutically acceptable active ingredient that treats disorders characterized by recurring attacks of motor, sensory, or psychic malfunction with or without unconsciousness or convulsive movements. Non-limiting examples of anti-epileptic compounds having analgesic activity include gabapentin, pregabalin, carbamazepine, lamotrigine, phenytoin, fosphenytoin, and analogues thereof.

The term "pain alleviating properties" is generally defined herein to include the expressions "pain-suppressing," "pain-reducing", and "pain-inhibiting" as the invention is applicable to the alleviation of existing pain, as well as the suppression or inhibition of pain which would otherwise ensue from the imminent pain-causing event.

In a preferred embodiment of the present invention, anti-epileptic compounds having pain alleviating properties include those that have the following Formula I:

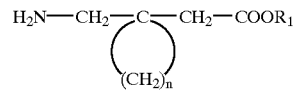

wherein $R_1$ is hydrogen or a lower alkyl; n is an integer of from 4 to 6; and the cyclic ring is optionally substituted, and the pharmaceutically acceptable salts thereof. The term lower alkyl includes straight or branched chain alkyl groups of up to eight carbon atoms. An especially preferred embodiment utilizes a compound of Formula I where $R_1$ is hydrogen and n is 5, which compound is 1-(aminomethyl)-cyclohexane acetic acid, known generically as gabapentin.

Other preferred compounds of Formula I above include, but are not limited to, ethyl 1-aminomethyl-1-cyclohexane-acetate, 1-aminomethyl-1-cycloheptane-acetic acid, 1-aminomethyl-1-cyclopentane-acetic acid, methyl-1-aminomethyl-1-cyclohexane-acetate, n-butyl 1-aminomethyl-1-cyclohexane-acetate, methyl 1-aminomethyl-1-cycloheptane-acetate, n-butyl 1-aminomethyl-1-cycloheptane-acetate, toluene sulfonate, 1-aminomethyl-1-cyclopentane-acetate, benzene-sulfonate, and n-butyl 1-aminomethyl-1-cyclopentane-acetate.

Other preferred compounds of Formula I above, wherein the cyclic ring is substituted for example with alkyl such as methyl or ethyl, include, but are not limited to (1-aminomethyl-3-methylcyclohexyl)acetic acid, (1-aminomethyl-3-methylcyclopentyl)acetic acid, and (1-aminomethyl-3,4-dimethylcyclopentyl)acetic acid.

In another preferred embodiment of the present invention, anti-epileptic compounds having pain alleviating properties include those that are included in Formula II:

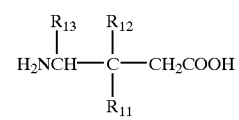

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual diastereomeric or enantiomeric isomer thereof, or a pharmaceutically acceptable salt thereof.

The most preferred compound of Formula II is where $R_{12}$ and $R_{13}$ are both hydrogen, and $R_{11}$ is —$(CH_2)_{0-2}$-i$C_4H_9$ as an (R), (S), or (R,S) isomer. A more preferred embodiment of the invention utilizes 3-aminomethyl-5-methylhexanoic acid, and especially (S)-3-(aminomethyl)-5-methylhexanoic acid, now known generically as pregabalin. Another preferred compound is 3-(1-aminoethyl)-5-methylhexanoic acid.

In the preferred embodiment of the present invention, the combination will be comprised of compounds of Formula I in combination with the compound selected from the group consisting of NSAIDs, analgesics, and NMDA receptor antagonists. In a more preferred embodiment of the present invention, the combination will contain the compound, gabapentin, as the anti-epileptic drug.

In addition to its pain alleviating properties, gabapentin is extremely well-tolerated and has been demonstrated to be virtually free of drug interactions. The unique properties and mechanism of action of anti-epileptic compounds like gabapentin, which demonstrate pain alleviating properties, would allow it to be used in the combinations described above with the benefit of providing better pain relief than if it were used not in combination. An added benefit of using the combination would be to use reduced quantities of medication, thereby potentially reducing adverse events for the patient.

The amount of the active ingredients in the combinations will vary depending on the mammal to which the combinations are administered, the type of pain to be treated, other active ingredients present, etc. Generally, the amount of the anti-epileptic compound(s) and the other active compound for a given composition and dosage form can be readily determined employing routine procedures.

The present invention is also directed to methods of treating mammals to alleviate pain by the co-administration of an anti-epileptic compounds that have pain alleviating properties and a compound selected from the group consisting of analgesics, NSAIDS, and NMDA receptor antagonists. The types of treatable pain experienced by mammals is varied and known to medical practitioners. Non-limiting examples of mammalian pain include centrally mediated pain, peripherally mediated pain, structural or soft tissue injury related pain, progressive disease related pain (i.e., oncology) and neuropathic pain states, all of which would include both acute (i.e., acute injury or trauma, pre and post-surgical, headache such as a migraine), chronic (i.e., neuropathic pain conditions such diabetic peripheral neuropathy and post-herpatic neuralgia) and inflammatory condition (i.e., osteo or rheumatoid arthritis, sequela to acute injury or trauma) pain states.

Pharmaceutical compositions containing the combination of the present invention or its salts are produced by formulating the active compound in dosage unit form with a pharmaceutical carrier. Some examples of suitable dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin, sorbitol; polyethylene glycol; water, agar, alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other suitable pharmacologically active components.

Preferred routes of administration of the subject combinations are oral or parenteral. Dosing will vary depending upon the mammal and a number of other factors.

EXAMPLES

Example 1

The aim of this experiment was to characterize the antinociceptive and anti-inflammatory effects of gabapentin administered in combination with a prototypic NSAID in the rat. In this example, gabapentin, naproxen sodium, and the combination of gabapentin and naproxen sodium were evaluated in a standard rat carrageenan footpad thermal hyperalgesia assay. This assay utilizes an extract of seaweed (carrageenan) that, when injected into the footpad of test animals, causes a sterile inflammation, thereby lowering the pain threshold. Anti-epileptic agents having analgesic properties, such as gabapentin, raise the pain threshold back to normal, thereby enabling the animal to tolerate an external source of pain for a longer period of time relative to untreated control animals.

Figure 2:
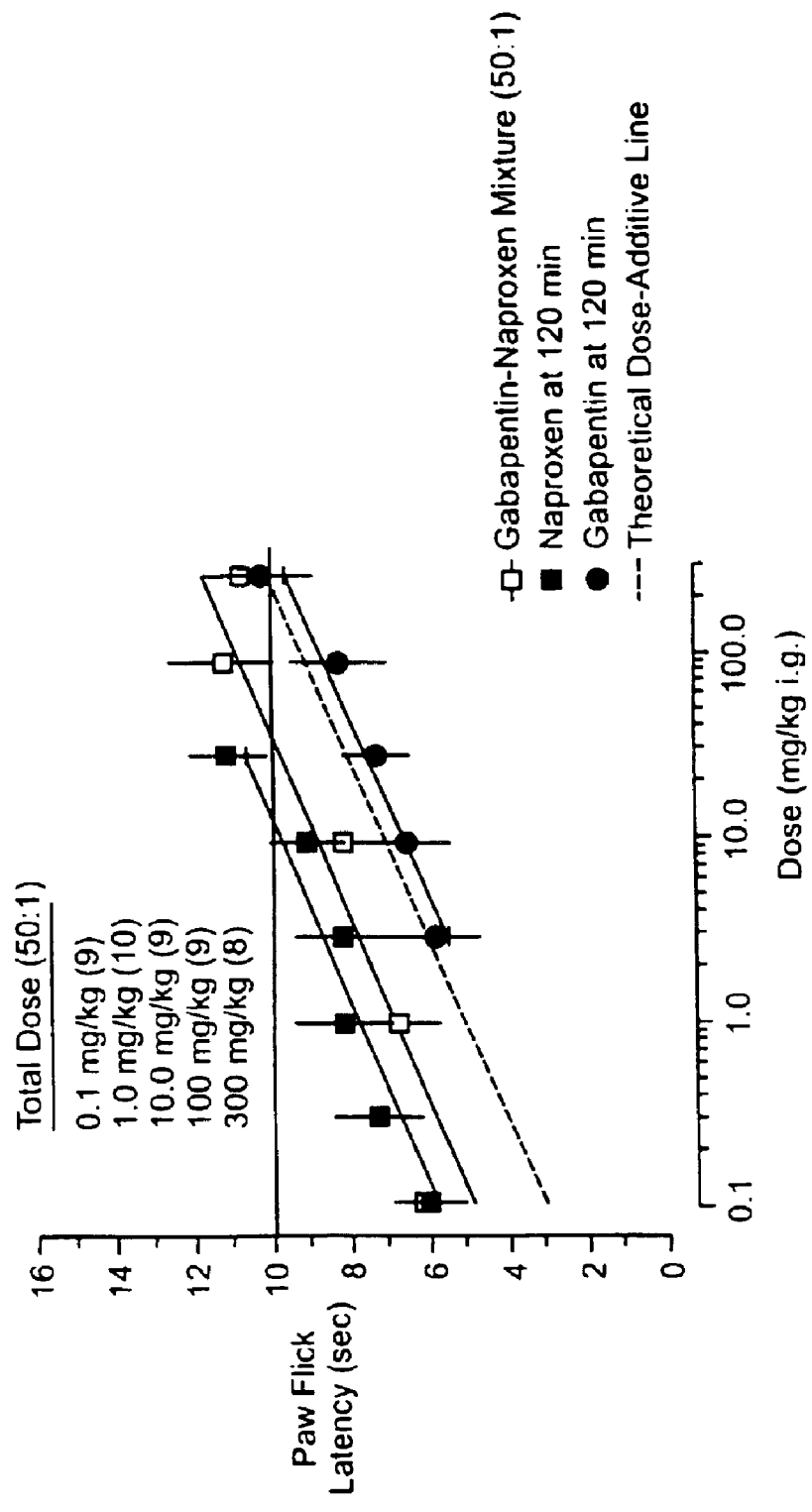
FIG. 2 shows the anti-hyperalgesic actions of fixed 50:1 (50 parts by weight of gabapentin to 1 part by weight of naproxen sodium) combinations of gabapentin and naproxen sodium at various dosages.

As shown in FIG. 1, gabapentin and naproxen sodium were given alone (gabapentin at 120 min after dosing; naproxen sodium at 120 min after dosing). Each data point represents the mean and standard error of mean. Data for each drug were fitted by least squares linear regression to a straight line. The theoretical dose-additive line for a 1:1 dose ratio was determined (dotted line) as described (Tallarida, 1992). The experimental determination of a 1:1 dose ratio was determined (gabapentin-naproxen sodium mixture 1:1) and was found to be significantly different than the theoretical dose-additive line. Thus, a supra-additive effect was determined for the combination of the two treatments given simultaneously. As shown in FIG. 2, the experiment was performed as described in FIG. 1 and similarly a supra-additive effect was determined for the combination of the two treatments given simultaneously, except that the theoretical dose-additive line (dotted line) and experimental data (open boxes) were both determined for a 50:1 ratio of gabapentin dose to naproxen sodium dose.

To summarize, the data showed that both gabapentin (3–100 mg/kg PO) and naproxen sodium (0.3–30 mg/kg PO) caused anti-hyperalgesic actions in the rat carrageenan footpad model (Hargreaves test). Combinations in a fixed ratio (1 mg gabapentin/1 mg naproxen sodium or 1:1 ratio) were anti-hyperalgesic, and produced a significantly supra-additive effect (synergistic action). For example, with a 1:1 dose ratio, dosages of naproxen sodium (0.05 mg/kg) plus gabapentin (0.05 mg/kg) that were both less than 1/10th of the $ED_{50}$ dose of the respective compounds alone, produced maximal antihyperalgesic effects when given in combination (see Table 1). Combinations in a fixed ratio (50 mg gabapentin/1 mg naproxen sodium) also were anti-hyperalgesic, with a significant tendency towards a greater than additive effect.

The data establish that the combination of gabapentin and naproxen sodium is synergistic in its ability to relieve acute and chronic pain. The data also establish that the most preferred combination of gabapentin plus naproxen sodium is in a fixed-ratio combination near 1:1 (within some reasonable limit).

TABLE 1

$ED_{50}$ VALUES DETERMINED FOR GABAPENTIN, NAPROXEN AND TWO FIXED-RATIO COMBINATIONS IN THE CARRAGEENAN RAT FOOTPAD THERMAL HYPERALGESIA TEST.

| DRUG TREATMENT | $ED_{50}$† |
| --- | --- |
| Gabapentin | 17 mg/kg (2.4–46 mg/kg)† |
| Naproxen sodium | 0.36 mg/kg (0.007–1.26 mg/kg)† |
| Theoretical 1:1 | 0.7 mg/kg combined total |
| (gabapentin:naproxen) | [0.35 mg/kg gabapentin plus 0.35 mg/kg naproxen] |

TABLE 1-continued

ED$_{50}$ VALUES DETERMINED FOR GABAPENTIN,
NAPROXEN AND TWO FIXED-RATIO COMBINATIONS
IN THE CARRAGEENAN RAT FOOTPAD THERMAL
HYPERALGESIA TEST.

| DRUG TREATMENT | ED$_{50}$† |
|---|---|
| Experimental 1:1 (gabapentin:naproxen) | 0.00022 mg/kg combined total (n.d.—0.0020)† [0.00011 mg/kg gabapentin plus 0.00011 mg/kg naproxen]** |
| Theoretical 50:1 (gabapentin:naproxen) | 9.0 mg/kg combined total [8.8 mg/kg gabapentin plus 0.18 mg/kg naproxen] |
| Experimental 50:1 (gabapentin:naproxen) | 0.77 mg/kg combined total (0.06–3.18 mg/kg)† [0.75 mg/kg gabapentin plus 0.015 mg/kg naproxen]* |

†95% confidence limits of experimental ED$_{50}$ values are shown in parentheses.
*Significantly less than additive theoretical combined ED$_{50}$, $p < 0.05$.
**Significantly less than additive theoretical combined ED$_{50}$, $p < 0.001$.
n.d.—not determined Methods Animals Male Sprague-Dawley rats (200–250 g, Sasco Laboratories) were used. Rats were group housed 5/cage on a 12-hour light:dark cycle with free access to food and water. Rats received only one dose of a drug or drug combination. All drugs were administered orally by gavage.

Experimental Design

Dose-effect curves were first determined for (1) gabapentin by itself and (2) a prototypic NSAID (e.g., naproxen) by itself The ED$_{50}$ value and 95% confidence limits of each agent was determined, as was the time to peak effect. After determination of these values, dose effect curves were generated for gabapentin administered in a fixed dose ratio with the NSAID; the drugs were administered so that their peak effects were coincident. ED$_{50}$ values and 95% confidence limits were then determined for the drugs in combination.

Measures of Antinociception

Carrageenan-induced thermal hyperalgesia: Rats were acclimated to a testing chamber whose glass floor was maintained at 25° C. Thirty minutes later, a high intensity beam of light was focused through the glass on the ventral surface of each hindpaw, and the latency to reflex withdrawal of the paw from the light beam was measured to the nearest 0.1 second. This latency was termed the paw flick latency (PFL). Two measurements of PFL spaced 20 minutes apart were made for each paw, and the second measurement was taken as the baseline response latency. After determination of baseline PFL, 100 μL of 2% lambda-carrageenan was injected in the plantar surface of one hindpaw and the animal returned to the testing chamber. Two hours later, when thermal hyperalgesia was maximal and stable, either vehicle, gabapentin, naproxen, or gabapentin and naproxen was administered by gavage. Response latencies for the ipsilateral and contralateral hindpaws were then redetermined 15, 30, 45, 60, 90 and 120 minutes later. Data for further analysis were taken 120 minutes after oral dosing.

Statistical Analysis

Data were expressed as the mean ±SEM. Two-way analyses of variance for repeated measures was used to compare the effects of drug to that of vehicle. Dose-effect lines for gabapentin and the NSAID were constructed using individual data and fitted with least squares linear regression analysis to determine ED$_{50}$ values and 95% confidence limits. A similar analysis was conducted for the drugs in combination using the total dose administered. Since parallel dose-effect lines were obtained for gabapentin, naproxen, and the combination of gabapentin and naproxen, then a parallel line assay was conducted as described by Tallarida (Tallarida, 1992; Tallarida, et al; 1989). This analysis compared the position of the experimentally-derived dose-effect line for the combination to the position of the theoretical dose-additive line. A significant shift to the left or the right of the theoretical dose-additive line indicates that the drugs interacted in a supra-additive (synergistic) or an infra-additive manner (antagonistic), respectively.

The preceeding examples were presented so that the present invention may be better understood and are intended for purposes of illustration only and should not be construed to limit the scope of the invention, as defined by the claims appended hereto.

What is claimed is:

1. A combination of an effective amount of an anti-epileptic compound having pain alleviating properties and a compound which is a NMDA receptor antagonist, wherein the anti-epileptic compound is a compound of Formula II

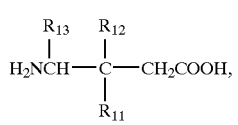

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxcyl; or an individual diastereomeric or enantiomeric isomer thereof; or a pharmaceutically acceptable salt thereof.

2. The combination according to claim 1, wherein the anti-epileptic compound is pregabalin.

3. A pharmaceutical composition, comprising a combination of an effective amount of an anti-epileptic compound having pain alleviating properties and a compound which is a NMDA receptor antagonist, together with a pharmaceutically acceptable carrier, wherein the anti-epileptic compound is a compound of Formula II

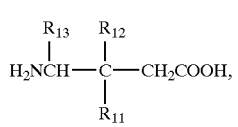

wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual diastereomeric or enantiomeric isomer thereof; or a pharmaceutically acceptable salt thereof.

4. The pharmaceutical composition according to claim 3, wherein the anti-epileptic compound is pregabalin.

5. A method for treating acute pain in a patient in need of treatment, comprising administering to the patient an acute pain relieving amount of an anti-epileptic compound having pain alleviating properties and a compound which is a NMDA receptor antagonist, wherein the anti-epileptic compound is a compound of Formula II

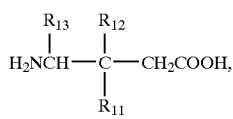

II wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual diastereomeric or enantiomeric isomer thereof; or a pharmaceutically acceptable salt thereof.

6. The method of treatment according to claim 5, wherein the anti-epileptic compound is pregabalin.

7. A method for treating chronic pain in a patient in need of treatment, comprising administering to the patient an chronic pain relieving amount of an anti-epileptic compound having pain alleviating properties and a compound which is a NMDA receptor antagonist, wherein the anti-epileptic compound is a compound of Formula II

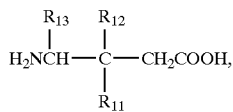

II wherein $R_{11}$ is a straight or branched alkyl of from 1 to 6 carbon atoms, phenyl, or cycloalkyl having from 3 to 6 carbon atoms; $R_{12}$ is hydrogen or methyl; and $R_{13}$ is hydrogen, methyl, or carboxyl; or an individual diastereomeric or enantiomeric isomer thereof; or a pharmaceutically acceptable salt thereof.

8. The method of treatment according to claim 7, wherein the anti-epileptic compound is pregabalin.

9. A method for treating inflammatory pain in a patient in need of treatment, comprising administering to the patient an inflammatory pain relieving amount of an anti-epileptic compound having pain alleviating properties and a compound which is a NMDA receptor antagonist, wherein the anti-epileptic compound is a compound of Formula II

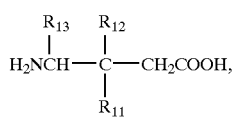

II wherein $R_{11}$ is a straight or branched alkyl of from 1 to 6 carbon atoms, phenyl, or cycloalkyl having from 3 to 6 carbon atoms $R_{12}$ is hydrogen or methyl; and $R_{13}$ is hydrogen, methyl, or carboxyl; or an individual diastereomeric or enantiomeric isomer thereof; or a pharmaceutically acceptable salt thereof.

10. The method of treatment according to claim 9, wherein the anti-epileptic compound is pregabalin.

* * * * *